United States Patent [19]
June et al.

[11] Patent Number: 5,777,180
[45] Date of Patent: Jul. 7, 1998

[54] PROCESS FOR THE PRODUCTION OF BISPHENOLS

[75] Inventors: Raymond Lawrence June; Robert Lawrence Blackbourn, both of Houston; Edgar Donald Allan, Katy; James Laurel Buechele, Houston, all of Tex.

[73] Assignee: Shell Oil Company, Houston, Tex.

[21] Appl. No.: 773,805

[22] Filed: Dec. 18, 1996

Related U.S. Application Data

[60] Provisional application No. 60/008,849 Dec. 19, 1995.
[51] Int. Cl.$^6$ .................................................. C07C 39/12
[52] U.S. Cl. ........................... 568/728; 568/727; 568/722
[58] Field of Search .................................... 568/728, 727, 568/722

[56] References Cited

FOREIGN PATENT DOCUMENTS

06/092889  5/1994  Japan.
1410750  10/1975  United Kingdom.

*Primary Examiner*—Gary Geist
*Assistant Examiner*—Jafar Parsa
*Attorney, Agent, or Firm*—Todd F. Volyn

[57] ABSTRACT

An improved process for the production of bisphenols is presented in which ketones and phenols are reacted in the presence of an acidic cationic exchange resin catalyst and a mercaptan cocatalyst. Prior to the reaction, alkyl alcohol is removed from the ketone stream. Cocatalyst is withdrawn from the reactor so that cocatalyst derivatives such as disulphide ions can be removed from the presence of the catalyst thereby reducing the possibility of catalyst poisoning.

14 Claims, 1 Drawing Sheet

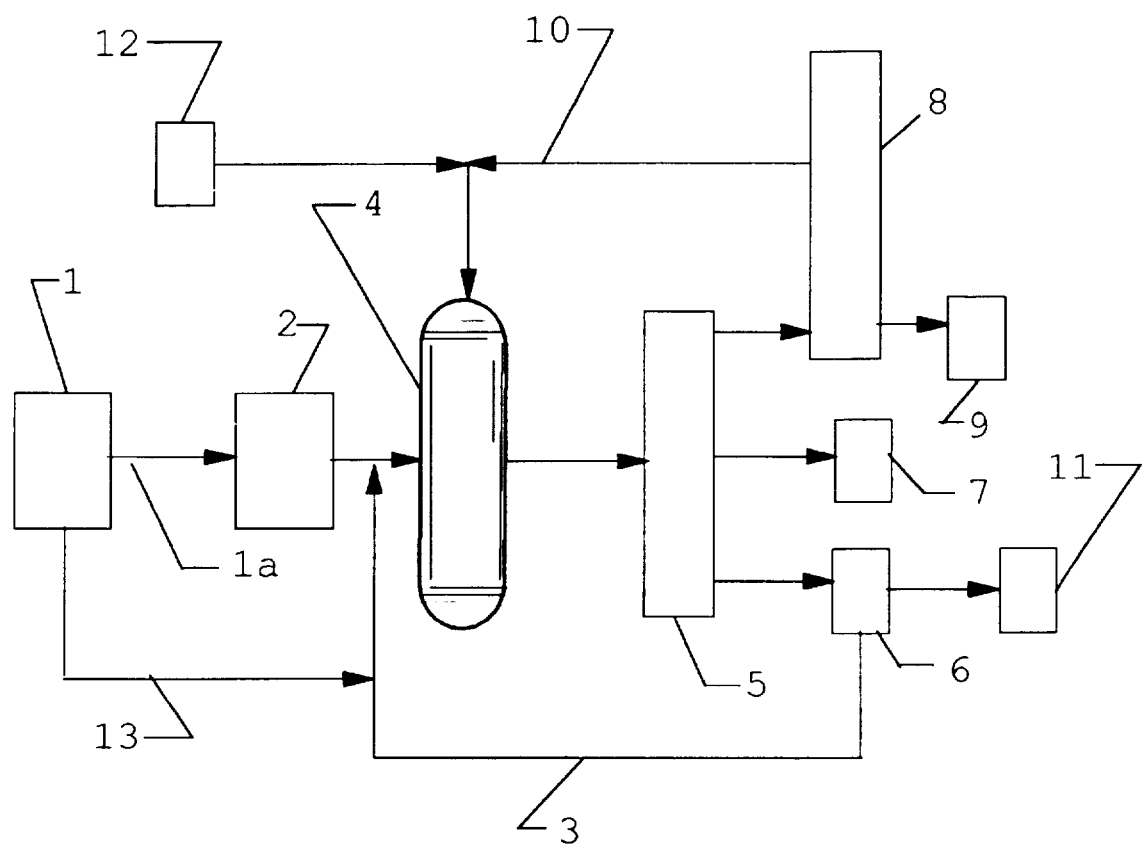

PROCESS FOR THE PRODUCTION OF BISPHENOLS

FIELD OF THE INVENTION

This application claims the benefit of the filing of U.S. Provisional patent application Ser. No. 60/008,849 filed on Dec. 19, 1995 relating to the production of bisphenols. More particularly, this invention relates to a process for the production of 2,2-bis(4-hydroxyphenyl) propane (also known as bisphenol A, hereafter "BPA") from acetone and phenol.

BACKGROUND OF THE INVENTION

Bisphenols are used as raw materials in the preparation of chemical products such as epoxy resins and polycarbonates. They are commonly prepared by the condensation of phenols and ketones. BPA is among the most important of the bisphenols. It is well known that BPA can be produced by reacting acetone (also known as dimethyl ketone, hereafter "DMK") and phenol in the presence of an acid. Often, an additional cocatalyst is used in the reaction.

The reactants used in the production of BPA can come from a number of sources. This can introduce varying types and quantities of impurities and trace materials in bisphenol production feed. For example, DMK can be produced from the oxidation of isopropyl alcohol (IPA) or by the decomposition of cumene hydroperoxide. DMK produced from the oxidation of IPA is called "on purpose DMK" and is known to be low in certain impurities such as methanol. It is not widely produced on a commercial basis. Most bisphenol is produced in integrated chemical manufacturing plants and utilizes DMK manufactured during the decomposition of cumene hydroperoxide. DMK produced in this manner is typically found mixed with at least about 200 ppm methanol which will azeotrope with DMK.

A number of acidic catalysts can also be used in bisphenol production processes. In recent years, acidic cation exchange resins have become the overwhelming choice. Strongly acidic sulfonated polystyrene ion exchange resins are particularly useful in this regard.

Two different techniques for employing acidic ion exchange resins as catalysts predominate in industrial practice. In one technique (hereafter, "the free cocatalyst technique") cocatalyst is freely circulated in the reactor with the reaction feed. It is used to enhance the selectivity and/or activity of the reaction. An organic mercaptan such as methyl or ethyl mercaptan is typically used as the freely circulating cocatalyst in this technique. The acidic sites of the resin are left available, that is, largely unbound to cocatalyst. This provides flexibility in adjusting the optimal concentration of cocatalyst given the particular reaction conditions in question.

In the free cocatalyst technique, the cocatalyst can be put in the presence of reactants and catalyst in a number of ways and can be readily replenished as needed. This enables refinement of the reaction through the differential treatment of the catalyst and cocatalyst. If, for example, cocatalyst is removed from the reactor along with reactor products, it can be separated from the reaction products and recycled back into the reactor in a subsequent step. However, if a catalyst problem is encountered, the catalyst may be treated without necessarily involving any adjustments to the cocatalyst. While this is an advantage of the free cocatalyst method, it must also be acknowledged that it nevertheless introduces more variables into process control than might otherwise be encountered and makes for somewhat complex reaction dynamics.

In the second technique for employing acidic ion exchange resins in the production of bisphenols (hereafter, "the fixed modified resin technique"), the resin is modified by appending cocatalytic agents such as aminoalkylmercaptans to some of the acid sites on the resinous catalyst. Typically, organo mercaptan promoter groups are attached to the backbone sulfonate ion by covalent or ionic nitrogen linkages. The fixed modified resin technique requires less direct handling and treatment of cocatalysts such as the noxious mercaptans. The ability to refine the process by differential treatment of the resin and cocatalyst is greatly reduced but there are fewer possibilities for the source of problems and reaction dynamics are less complicated than is seen in the free cocatalyst technique.

The acidic catalysts used in either technique have shown a tremendous proclivity for rapid deactivation. There are many possible reasons for this including catalyst poisoning. As noted above, any number of materials other than phenols and ketones may be present in the feed and could interfere with the catalyst. For example, metal poisoning is a possibility in large scale industrial processes of this type. Additionally, thermal perturbations can cause a loss of the acidic functional groups from the resins on which they are supposed to be bound. Further, the presence of bisphenolic tars and other reaction residuals can greatly reduce mass transfer in the reaction.

European Patent 567857 A1 assigned to Bayer AG listing inventors Klaus Berg, et. al. is directed to the production of bisphenols from phenols and carbonyl compounds using a fixed modified resin technique. The catalytic exchange resin is a sulfonated polystyrene ion exchange resin modified with an aminomercaptan. The inventors found catalyst life to be insufficient and proposed as a solution using a feed containing less than 100 ppm of alkylating agent (alkyl alcohol). When feed contains more than this concentration of alkylating agent the SH group on the free end of the aminomercaptan becomes an SC or an SCC group thereby substantially diminishing its function as a leaving group and directly poisoning the exchange resin. When the following reaction (and other similar reactions) occurs, the catalyst is poisoned.

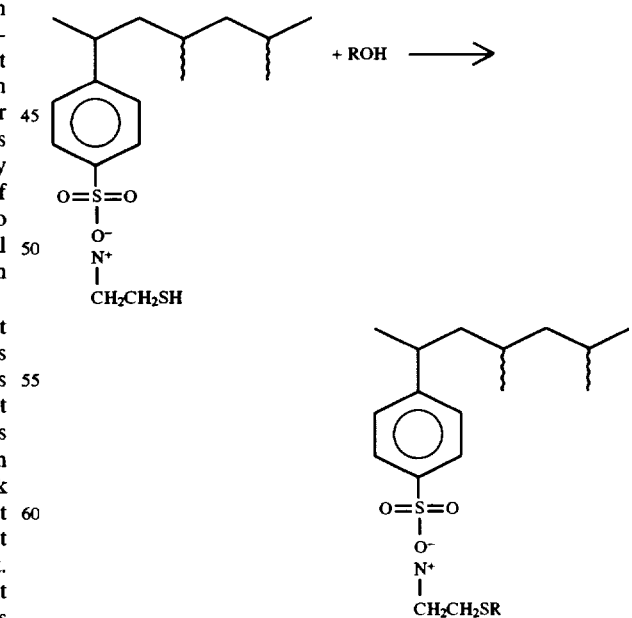

In the instant invention, the inventors address the premature deactivation of catalyst in a free cocatalyst process for the production of bisphenol. If one were to apply the rationale of EP 567857 A1 to the free cocatalyst method they would expect catalyst deactivation to be the result of the production of esters due to the reaction of sulfonic acid groups on the resin with alkyl alcohols.

However, the inventors have found that catalyst deactivation is not appreciably attributable to ester formation. Moreover, conducting the process at the alkyl alcohol concentration proposed in EP 567857 A1 would still result in substantial catalyst deactivation. Clearly, the catalyst deactivation mechanism experienced in the free cocatalyst method differs from that of the fixed modified resin method. Thus, in the instant invention, different process parameters and methods for reducing or eliminating the premature deactivation of catalyst are presented.

Japanese Patent Publication 6-92889 of Apr. 5, 1994 with listed inventors Nakawa, Kanbara, and Nosei proposes a process for producing BPA by the condensation of DMK and phenol in which the concentration of methanol in the DMK feed is kept below 10,000 ppm. This is done by recirculating unreacted DMK back to the feed after some of the methanol in the unreacted DMK is purged out of the reactor product stream. The mixture of fresh DMK and DMK obtained through the separation tower apparently will never contain less than about 400 ppm methanol. The purpose of this process is to directly control the acidity of the catalyst. While they describe their invention as ameliorating the "deterioration" of the catalyst, no information is presented regarding the effect of lowering methanol concentration over time. Rather, a higher one pass conversion to useful products is presented. This makes it clear that Nakawa et. al. were not addressing a catalyst poisoning mechanism but were instead maintaining the effective acidity of the reaction/catalyst. At the more optimal level with respect to catalyst activity. Adding excess water would have the same type of effect.

The free cocatalyst method for producing bisphenols could be improved through the amelioration of the catalyst poisoning reaction. Since the free cocatalyst and fixed modified resin techniques deactivate catalyst differently, new process steps, parameters, and conditions are necessary to provide such an improvement.

SUMMARY OF THE INVENTION

An improved process for the production of bisphenols is presented. The process is a free cocatalyst process in which the methanol content in the feed is reduced to less than about 50 ppm and in which cocatalyst conversion to harmful suflidic derivatives is ameliorated through the use of purges or other withdrawal means.

In one aspect of this invention, a process for the production of BPA is presented comprising the steps of:

a) removing alkyl alcohol from a feed stream of DMK and phenol to a concentration of less than about 50 ppm;

b) reacting a said feed stream in a reactor in the presence of a acidic ion exchange resin catalyst and a cocatalyst comprising an alkylmercaptan to form a product mixture comprising BPA, phenol, DMK, water, methanol, and cocatalyst and cocatalyst derivatives;

c) separating the components of said product mixture;

d) returning cocatalyst separated from said product mixture to said reactor;

e) returning DMK and phenol separated from said product mixture to said feed stream; and f) recovering BPA.

In yet another aspect of this invention the alkyl alcohol is methanol the removal of which provides a feed stream comprising DMK and phenol with a concentration of less than about 10 ppm.

In yet another aspect of this invention, the alkyl alcohol removal step comprises distillation.

In yet another aspect of this invention, the alkyl alcohol removal step comprises adsorption.

In yet another aspect of this invention, the process is conducted as part of an integrated chemical manufacturing process wherein phenol and DMK reactants are produced from the decomposition of cumene hydroperoxide.

BRIEF DESCRIPTION OF THE DRAWING

The figure is a schematic diagram of the process of the invention.

DETAILED DESCRIPTION OF THE INVENTION

We have found that the production of certain sulfides formed from the mercaptan cocatalysts used in the free cocatalyst technique can result in rapid deactivation of acidic ion exchange resins used in the production of bisphenols. Removal of intermediates that lead to the production of these sulfides and reduction or elimination of feed impurities greatly reduces the loss of catalyst activity over time. This is best exemplified when the catalyst is a sulfonated polystyrene catalyst and the co-catalyst is methylmercaptan (MeSH). In such cases it has been found that an ordinary feed containing about 200 ppm methanol reacts with the MeSH to form dimethylsulfide (DMS) and water. The DMS then reacts again with additional methanol to form a trimethylsulfonium cation (TMS). A proton is also consumed in this reaction. It is the TMS ion which quantitatively ties up the proton on the acid site on the resin. This process can be depicted as follows:

$$H_3CSH + CH_3OH \xrightarrow{H^+} (CH_3)_2S + H_2O \text{ (DMS FORMATION)} \quad 1.$$

$$(CH_3)_2S + CH_3OH + \xrightarrow{H^+} (CH_3)_3S^+ + H_2O \text{ (TMS FORMATION)} \quad 2.$$

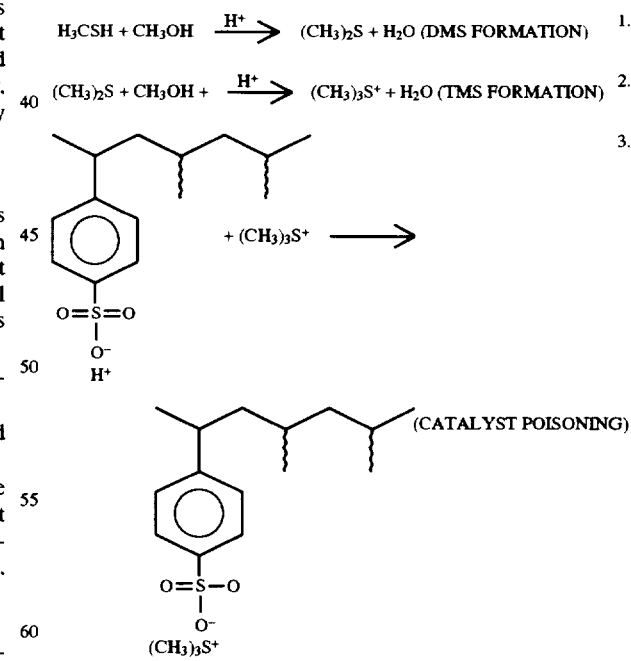

In the fixed modified resin technique, catalyst deactivation results from the direct alkylation of the catalyst modifier attached to the resin. That is, the hydroxyl group of an alkyl alcohol condenses with the terminal hydrogen of the modifier to form water. The alkyl group then directly alkylates the modifier interfering with the subsequent synthesis of BPA. Thus, alkylation poisons the catalyst directly and cannot be ameliorated by adjustment or treatment of a cocatalyst or cocatalyst derivatives.

In the process of this invention, bisphenols are produced by the condensation of a ketone with stoichiometric excess of a phenol or a phenolic derivative. Reactants are supplied to a reactor in two feed streams comprising a ketone stream and a phenolic stream respectively. Alkyl alcohol, typically methanol, is removed from the ketone stream. Mercaptan cocatalyst is also added to the reactor as a feed stream. The reactants are introduced into a reactor wherein the temperature is from about 40° C. to about 95° C. Catalyst and cocatalyst are, of course, also present in the reactor. The pressure within the reactor may be ambient or within the range of 1–10 atmospheres. Within the reactor, bisphenols are then formed and are discharged as part of a product stream. The product stream comprising bisphenol, unreacted ketone, water, mercaptan cocatalyst, methanol, and unreacted phenol is then sent to a separator. Bisphenol and unreacted phenol is removed as a bottoms product while water and some residual methanol that may be present is withdrawn as a side draw. Ketone, mercaptan cocatalyst, and remaining methanol are withdrawn as tops products and are recirculated back to the reactant/feed stream.

Extension of catalyst life or reduction in catalyst deactivation is achieved by the practice of the following steps. Alkyl alcohols are removed from the feed stream prior to the reaction. Cocatalyst and cocatalyst derivatives are removed from the reactor with reactor products and subsequently separated; harmful cocatalyst derivatives such as dimethylsulfide can then be purged from the process. This allows cocatalyst without harmful derivatives to be returned to the reactor. Alternatively, cocatalyst and cocatalyst derivatives can simply be replaced by fresh cocatalyst. Unreacted alkyl alcohol is also removed as a side draw (along with water) from the separated product mixture so that recycle streams do not add any significant quantity of alkyl alcohols to the reactor. Including these steps can, and typically will, lengthen the life of the catalyst fourfold. That is, the catalyst can be left on stream and without a significant loss in activity or selectivity four times as long as a bisphenol production process in which these steps are not followed.

The typical ketone feed contains between about 2000–3000 ppm water and about 150–300 ppm methanol. Up to about 10,000 lbs of ketone per hour are typically processed in this manner. Alkyl alcohol (principally methanol) is removed from the feed stream by any of the well known methods such as distillation. In the typical case of an integrated chemical manufacturing facility, the alkyl alcohol is found only in the ketone feed. Usually this will require an azeotrope separation. This is the case when the ketone is DMK and the alkyl alcohol is methanol. Such azeotrope separations are well understood and easily achieved with techniques known in the art. Use of distillation as the separation technique can readily reduce the methanol concentration in the DMK feed to less than about 50 ppm. Ketone feeds having less than about 50 ppm methanol are substantially methanol free for the purpose of practicing this invention.

Another method for the removal of alkyl alcohols is through adsorption on a molecular sieve. In this method, a column is filled with zeolite such that about one bed volume of zeolite is used to treat up to about 25 volumes of DMK. Molecular sieves useful for this purpose have pore sizes of about 4–5 A. The "Type A" molecular sieve commercially available from Zeochem Inc. is the presently preferred molecular sieve. When alkyl alcohol is removed by the use of a molecular sieve, its concentration in the feed can be readily reduced to less than about 10 ppm.

The most preferred method for this removal involves a combination of azeotropic distillation and molecular sieves. In this manner a much smaller molecular sieve system can be emplaced on a concentrated alcohol stream produced by distillation. Alkylalcohol concentrations of less than about 10 ppm are readily achieved.

In general, the catalytic agents employed in this invention are sulfonated aromatic resins comprising hydrocarbon polymers having a plurality of pendant sulfonic acid groups. These are typically 2 or 4% divinyl benzene crosslinked. Sulfonated polystyrene, poly(styrenedivinylbenzene) copolymer, and sulfonated phenolformaldehyde resins have utility in this regard. Sulfonated polystyrene resin catalysts commercially available "K1131" brand catalyst from Bayer Chemical Company is the most preferred ion exchange resin for this purpose. The exchange capacity of the acidic resin is preferably at least about 2.0 meq. $H^+$/gram of dry resin. Ranges from 3.0 to about 5.5 meq $H^+$/gram of dry resin are most preferred.

Cocatalysts useful in this invention are comprised of alkyl mercaptans such as methyl mercaptan, ethyl mercaptan, propyl mercaptan. Methyl mercaptan is presently the preferred cocatalyst.

Turning now to the figure, upstream process 1 produces ketones and phenols (such as DMK and phenol) along with other minor components including alkyl alcohol such as methanol. One such upstream process is the cleavage of cumene hydroperoxide. Upstream process 1 is also understood to be the bisphenol reactant source.

Two different streams of reactants, a ketone stream 1a, and a phenol stream 13 are withdrawn from upstream process 1. The phenol stream is fed into reactor 4. The ketone stream is fed into alkyl alcohol removal vessel 2 where alkyl alcohol is removed from the stream. As noted above this can be done through distillation, zeolitic adsorption, or any other means known in the art provided that the method reduces the alkyl alcohol concentration below about 50 ppm and preferably below about 10 ppm.

Having had the alkyl alcohol concentration reduced to below about 50 ppm, the ketone stream is, together with phenol stream 13, fed into reactor 4. Feed stream volumes flowing into reactor 4 can be up to about 200,000 lbs per hour although, as one skilled in the art will readily appreciate, the feed rate is dependent upon the conditions in which the reaction is carried out. Reactor 4 can be a single reactor or can be a series of reactors and can be run in the up or downflow configuration. Preferably reactor 4 is operated at temperatures between about 40° C. and 95° C. and pressures between about 1 and 10 atmospheres. Reactor 4 is also charged with an acidic ion exchange resin catalyst of the type discussed above. Finally, reactor 4 is also charged with free mercaptan cocatalyst of the type discussed above. This cocatalyst is originally fed into the reactor from a cocatalyst source 12. Cocatalyst concentration is also controlled by the return (to either the reactor or the cocatalyst source 12) of cocatalyst which has been withdrawn from the product stream and separated from alkylated species. The cocatalyst return is shown as stream 10 in the figure.

The reactants in reactor 4 react to form bisphenol (BPA when the reactants are DMK and phenol) and leave the reactor 4 as a product stream comprising the bisphenol, unreacted reactants, cocatalyst, cocatalyst derivatives comprising primary alkylated mercaptans such as dimethyl sulfide, water, and a small amount of unreacted alkyl alcohol such as methanol. The product stream is fed into the separator 5 which can be any conventional method for separating such materials. Distillation is generally the simplest and most preferred method. However, other well known methods can be used independently or in combination with distillation to comprise this separation process.

When the separation is done as a distillation, the tops products will comprise the cocatalyst, cocatalyst derivatives, alkyl alcohol, and a small amount of other impurities. These tops products are contacted with phenol in the cocatalyst absorber column 8. In the cocatalyst absorber column 8, cocatalyst is absorbed from the rest of the tops products of separator 5 and is returned to the reactor via a cocatalyst return line 10. Cocatalyst derivatives such as dimethyl sulfide can simply be purged from the cocatalyst absorber along with other impurities such as alkyl alcohols. Those skilled in the art will appreciate that this purge can also be separated into constituents which can also find subsequent utility. These are withdrawn from the process in purge 9. This purge of cocatalyst derivatives such as DMS and methanol enable a fine sense of refinement by which the life of the catalyst in reactor 4 is further preserved.

Another purge can also be taken from separator 5 as middle distillate components comprising methanol and water. This occurs at purge 7 and can result in the removal of between about 10 and 25% wt of the total alkyl alcohol in the process at any one time.

The bisphenol product, bisphenol isomers, phenol, and a small amount of various impurities are removed from separator 5 as a bottoms product. This bottoms product is fed to a further separator 6. Crystallization is the preferred method of bisphenol separation but any method which can be used to separate bisphenol from the mother liquor can be used depending upon the desired degree of purity of the bisphenol product. Once separated, the mother liquor comprising phenol and bisphenol isomers is returned to the reactor 4 as reactant. It can thus be seen that recirculated phenol is free of alkyl alcohols and thus further enhances the life of the catalyst in the free cocatalyst method.

Bisphenol separated from mother liquor in separator 6 can then be sent to yet further separations and purifiers such as the bisphenol recovery process 11. This can be particularly important where very pure product is required as where BPA is produced for use in the subsequent production of polycarbonates. Generally, such further separations can be beneficially conducted using techniques such as recrystallization.

Thus it can be seen that by removing allyl alcohols from the feed, removing and adjusting cocatalyst concentration and the presence of harmful derivatives of cocatalyst, removing alkyl alcohol from downstream steps of the reaction, and controlling cocatalyst use, this free cocatalyst method of bisphenol production provides a number of flexible means for eliminating or reducing catalyst poisoning and thereby extending the life of the catalyst up to fourfold relative to processes which do not employ these steps.

This invention is further understood by reference to the following nonlimiting examples.

EXAMPLE 1

(Amelioration of Catalyst Poisoning)

A sulfonated polystyrene catalyst commercially available under the tradename "A-32" (a product of Rohm and Haas Chemical Co.)was left on stream in a BPA production process. The A-32 catalyst had a titratable acidity of about 5.3 meq $H^+$/gm when fresh. This process was a free cocatalyst process, used DMK and phenol obtained from a CHP cleavage process as the reactant feed source, and employed methyl mercaptan as the free cocatalyst. The process was run nearly continuously.

The reactant feed had greater than about 50 ppm methanol present throughout its operation and typically averaged about 200 ppm methanol content. Methanol was not removed from the process and no significant adjustment was made to the cocatalyst other than recirculation back to reactor. Catalyst samples were withdrawn from the reaction after six (6), eleven (11), and fifteen and one half (15.5) months. Each of the samples were subjected to standard titration methods to determine remaining acidity. The sample on stream for six months was found to have an acidity of 3.4 meq $H^+$/gm, the sample on stream for eleven months had a remaining acidity of 2.7 meq $H^+$/gm and the sample on stream for 15.5 months had an acidity of 2.4 meq $H^+$/gm.

The three samples were then tested to determine their ability to convert DMK in a BPA process using a stock solution. A sample of fresh catalyst was also tested in this process. The stock solution was prepared using about 5% wt DMK, 0.5% wt water, and 2.2% wt dodecanethiol with the balance being phenol. Dodecanethiol was used as the free cocatalyst. About 20 grams of stock solution was added to a 40 ml vial holding about 1 gram of catalyst sample therein. The vial was heated while a stirring bar was used to ensure uniform mixing. The reaction was conducted at 75° C. At a contact time equivalent to a $WHSV^{-1}$ of 13.3 hours, the DMK conversion for the fresh catalyst was about 82%, the conversion using the six month old sample was about 58%, the conversion using the 11 month old sample was about 36%, and the conversion using the 15.5 month old sample was about 28%.

This example illustrates the catalyst poisoning seen when the method of the instant invention is not employed in a free cocatalyst method for bisphenol production. The catalyst was regenerated with sulfuric acid and then returned the catalytic activity and titratable acid to acceptable operational levels. Solid state NMR analysis revealed that it was the trimethyl sulfonium ion that was removed from the catalyst upon regeneration.

EXAMPLE 2

(Computer Simulation of Methanol Removal by Distillation)

A distillation column is set up for the simulated separation of acetone and methanol from the ketone feed stream as shown in FIG. 1. The distillation column is illustrative of alkyl alcohol removal vessel, 2. Simulation of the separation is conducted using an ASPEN RADFRAC BLOCK computer model (available from Aspen Technology, Inc.). The feed enters the distillation column at the 33d plate and comprises about 0.02 w % methanol, 99.68 w % acetone, and 0.3 w % water. Flow rate is between about 10,000 and 15,230 lbs/hr. The column has 62 stages, a top stage temperature of about 57° C., a bottom stage temperature of about 62° C., and a molar reflux ratio of 19.712.

Reactor feed, 4 is withdrawn as column bottoms at the 47th stage plate and has a composition of about 99.66 w % acetone, 0.33 w % water, and 0.0005 w % methanol. The overhead composition is about 2000 ppmw methanol, 500 ppmw water, and remainder acetone. The reduction in the methanol concentration in reactor feed, 4 will increase catalyst life by 24–48 months on stream.

EXAMPLE 3

(Methanol Removal by Distillation and Zeolitic Adsorption)

The process of Example 2 was conducted by attaching a laboratory scale zeolitic bed (10"×1" tubing) to the top of the distillation column of Example 2. The vessel was packed with $\frac{1}{16}$" diameter, 5 Å pore size zeolite commercially available from UOP Corporation. The overhead of the distillation column then ran through the adsorbant containing vessel at a rate of about 1 bed volume per hour. Table 1 shows the methanol content of the effluent as a fraction of the methanol concentration entering the zeolite packed vessel ($C/C_0$).

TABLE 1

| Bed Volumes | $C/C_0$ |
|---|---|
| 20 | 0 |
| 23 | 0.0036 |
| 29 | 0.0275 |
| 32 | 0.525 |

Recombination of the effluent stream with the distillation column bottoms stream can then be conducted. This enables the recovery of about 10% of the initial process feed which could not otherwise be usefully used in the BPA production process. Thus, this example shows the dramatic improvement in economic efficiency achievable through this process.

What is claimed is:

1. A method for making bisphenol comprising:
   a) removing alkyl alcohol from a reactant stream comprising a ketone and a phenol such that said feed stream comprises less than 50 ppm of said alkyl alcohol;
   b) reacting said reactant stream in the presence of a cation exchange resin and a sulfur-containing cocatalyst to produce a reaction production comprising cocatalyst, cocatalyst derivatives, and a bisphenol liquor comprising bisphenol and phenol,
   d) separating said bisphenol from said reaction products,
   e) removing cocatalyst derivatives from said reaction products,
   f) returning cocatalyst to said reactor, and
   g) recovering bisphenol.

2. The method of claim 1 wherein the alkyl alcohol is removed from said methanol is removed by passage through a molecular sieve.

3. The method of claim 1 wherein said alkyl alcohol is present in said stream at a concentration of less than about 50 ppm after said alkyl alcohol removal step.

4. The method of claim 1 wherein said alkyl alcohol comprises methanol, said ketone comprises DMK, said phenol comprises phenol, and said bisphenol is BPA.

5. The method of claim 1 wherein said cation exchange resin is a sulfonated polystyrene and said cocatalyst is a mercaptan.

6. The method of claim 1 wherein said cocatalyst is methyl mercaptan.

7. The method of claim 2 wherein said molecular sieve has a pore size of about 4 to about 5 Å.

8. The method of claim 2 wherein alkyl alcohol is removed from said ketone by distillation and by passage through a molecular sieve.

9. A method for making bisphenol A comprising:
   a) feeding acetone produced as a product of a cumene production process to a methanol removal process to produce substantially methanol free acetone feed,
   b) reacting said acetone feed with phenol in the presence of an acidic cation exchange resin and a sulphur containing cocatalyst to produce BPA and effluent,
   c) removing cocatalyst and cocatalyst derivatives from said process,
   d) returning only the cocatalyst obtained from step c to said reaction, and
   e) separating said BPA from said effluent.

10. The method of claim 9 wherein less than about 10 ppm of methanol are present in step b.

11. The method of claim 9 wherein methanol is removed by azeotropic distillation.

12. The method of claim 10 wherein methanol is removed by passage through a molecular sieve.

13. The method of claim 10 wherein said cation exchange resin is selected from the group consisting of sulfonated polystyrene, poly(styrenedivinyl-benzene) copolymer, and sulfonated phenolformaldehyde resins and said cocatalyst is a mercaptan.

14. In a method for producing bisphenol A by reacting an acetone stream comprising methanol with a phenol stream in the presence of an acidic cation exchange resin and a sulphur containing cocatalyst, the improvement which consists of removing substantially all of the methanol from said acetone stream and eliminating alkylated cocatalyst derivatives from said reaction such that the acidic cation exchange resin is not poisoned.

* * * * *